United States Patent [19]

Getscher

[11] 4,379,451
[45] Apr. 12, 1983

[54] INTRAMEDULLARY HIP PIN AND CORTICAL PLATE

[76] Inventor: Philip E. Getscher, 4230 Burnham Suite 140, Las Vegas, Nev. 89109

[21] Appl. No.: 204,063

[22] Filed: Nov. 4, 1980

[51] Int. Cl.³ ............................................... A61F 5/04
[52] U.S. Cl. ........................... 128/92 CA; 128/92 BC; 411/38
[58] Field of Search ........ 128/92 BA, 92 BC, 92 CA, 128/336; 411/37, 38

[56] References Cited

U.S. PATENT DOCUMENTS

| | | |
|---|---|---|
| 2,396,501 | 3/1946 | Gibson ................................. 411/38 |
| 2,401,427 | 6/1946 | Kimbell ................................ 411/38 |
| 2,964,989 | 12/1960 | Croessant ........................... 411/38 |
| 4,236,512 | 12/1980 | Aginsky ........................ 128/92 BA |

*Primary Examiner*—Michael H. Thaler
*Assistant Examiner*—C. W. Shedd
*Attorney, Agent, or Firm*—Vincent L. Carney

[57] ABSTRACT

To receive the weight of the body from the pelvis and distribute it evenly to the shaft of a fractured femur while bracing the fractured femur, an intramedullary hip pin engages a plate secured to the lateral cortex of the shaft. The hip pin has an enlarged end portion positionable within the head and neck of the femur to receive and distribute forces from the pelvis and to impede protrusion of the pin through the head of the femur. The hip pin also includes an expansible member in the form of a cage for tightly securing the hip pin within the head and neck of the femur. The plate is adapted to be secured to the outer surface of the femur and includes an inclined, tubular, pin-receiving portion extending partially into an opening formed through the surface of the femur and into the neck of the femur.

2 Claims, 8 Drawing Figures

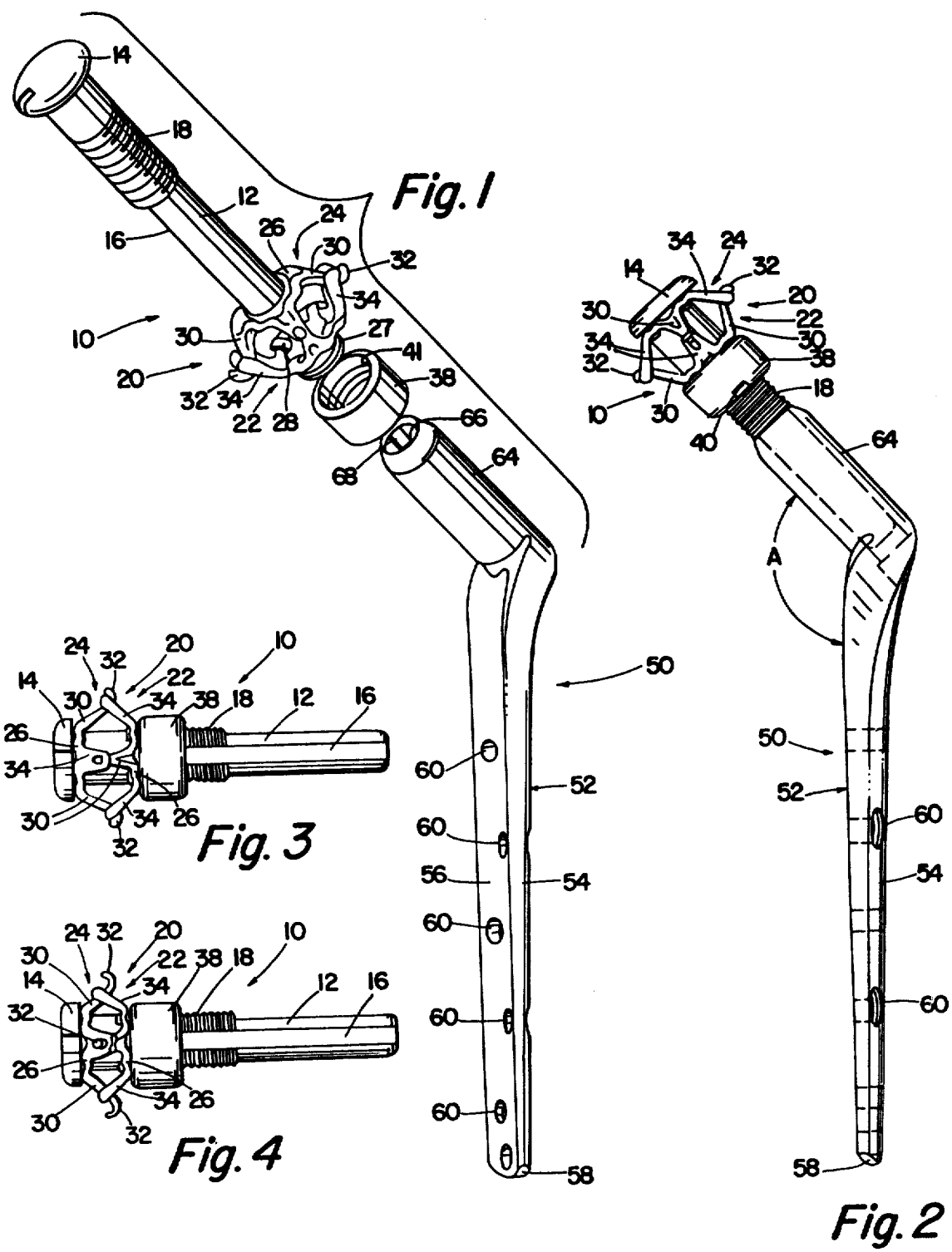

INTRAMEDULLARY HIP PIN AND CORTICAL PLATE

CROSS REFERENCE TO RELATED PATENT

INTERMEDULLARY HIP PIN, U.S. Pat. No. 3,918,441, issued Nov. 11, 1975, to Philip E. Getscher, here the "Hip Pin Patent," the disclosure of which is incorporated by reference.

BACKGROUND OF THE INVENTION

1. Field of the Invention

The present invention relates to hip pins and, more particularly, to an intramedullary hip pin and cortical plate especially adapted to resist loads and to permit weight to be applied without requiring long periods of healing.

2. Description of the Prior Art

A persistent problem with hip pins is that of preventing the hip pin from being forced through the head of the femur into the hip joint. As has been pointed out in the Hip Pin Patent, certain prior hip pins are in the form of narrow cones which extend through the neck of the femur on one end to a location adjacent the head. The pins are connected to plates extending along the femur and which are fastened thereto on the outside. Disadvantages of this type of prior hip pin construction include perforation of the head of the femur upon applying weight to the hip joint, poor distribution of forces from the pelvis which requires a relatively strong and large hip pin, and the inability to place weight on the fractured femur for an excessive period of time after the hip pin has been implanted.

The Hip Pin Patent represents an improvement over previous hip pin constructions. The pin includes a head portion having a saddle which corresponds substantially in shape to the neck of the femur so as to receive forces from the pelvis and distribute them relatively evenly. The head portion also includes a blunt nose facing the hip joint which resists movement of the head of the hip pin through the head of the femur. A shank formed substantially like a cone and having its pointed end downward is inserted into the medulla of the femur shaft and is secured to the head portion by a set screw.

Although the Hip Pin Patent represents an improvement over prior art devices, certain problems still have not been addressed. One of these problems relates to securing the hip pin within the head and neck of the femur so that not only is perforation of the head prevented, but rotation of the hip pin relative to the head and neck also is prevented. A continuing problem is that of anchoring the hip pin securely within the head and neck of the femur so that all relative movement between the hip pin and the femur is prevented.

An additional consideration which has not been adequately addressed by prior proposals relates to difficulties associated with inserting the hip pin into the head and neck of the femur and connecting the hip pin with a hip plate or shank. Complicated drilling and reaming operations sometimes are necessary, and it sometimes is difficult to properly maneuver the components of the hip pin assembly during implantation.

In view of the foregoing considerations, it is an object of the invention to provide a novel hip pin and coacting plate.

It is a further object of the invention to provide an intermedullary hip pin and cortical plate.

It is a still further object of the invention to provide a hip pin which resists being forced through the head of the femur.

It is a still further object of the invention to provide a hip pin which may be rigidly secured within the head and neck of the femur so that relative motion between the pin and femur is not possible.

It is a still further object of the invention to provide a hip pin and coacting plate requiring minimal drilling and manipulation of components for implantation.

SUMMARY OF THE INVENTION

In accordance with the above and further objects of the invention, the present invention provides an intramedullary hip pin and a cortical plate which fit together to hold the head and neck of the femur above the fractured portion to the shaft of the femur below the fractured portion. The hip pin includes a longitudinally extending shaft having an enlarged, flattened end. A groove extends longitudinally of the shaft, and a plurality of threads are provided near the mid-point of the shaft. The end of the pin is sufficiently large that it distributes forces applied through the pelvis, thereby tending to prevent the pin from perforating the head of the femur.

In order to prevent relative motion, including rotation, between the pin and the head and neck of the femur, an expansible member is carried by the pin. The member is in the form of a cage and includes opposed, interlocking sections having curved fingers. The sections are movable axially along the shaft, but rotation between the cage and the shaft is prevented by a bosses extending inwardly from the sections and engageable with the groove. A nut is engageable with the threaded portion and one of the sections. Upon tightening the nut sufficiently, the sections are clamped between the end of the pin and the nut, thereby compressing the sections. The cage thus is expanded and the fingers, being forced outwardly into the cancellous bone structure of the femur, cause the pin to be nonmovably secured to the portion of the femur above the fracture.

The plate includes an elongate section having openings formed for receiving screws. A tubular portion is located at one end of the elongate section and is positioned thereto at an angle of approximately 135 degrees. The tubular portion includes an inwardly projecting boss engageable with the longitudinal groove of the shaft. After the pin has been secured to the head and neck of the femur by expansion of the cage, the plate is attached to the pin by moving the tubular portion over the shaft. The elongate section of the plate is positioned along the lateral cortex of the shaft of the femur below the fractured portion and is secured thereto with multiple bone screws.

Due to the shape of the end of the hip pin and due to the expansion of the cage into the bone structure of the femur, forces applied from the pelvis are distributed well and all motion between the hip pin and the femur is prevented. Although the pin cannot rotate relative to the tubular portion of the plate, relative axial movement between them is possible. This allows telescoping of the pin into the tubular portion of the plate so as to keep bone fragments in contact as absorption of bone occurs during healing at the fracture site.

Insertion of the hip pin is exceedingly simple, requiring only a ½ inch hole to be drilled into the lateral cortex of the femur and through the neck of the femur and approximately one inch into the spherical portion of the head. Complex assembly steps during the implantation process are avoided entirely.

DESCRIPTION OF THE DRAWINGS

FIG. 1 is an exploded perspective view of a hip pin and cortical plate in accordance with an embodiment of the invention;

FIG. 2 is an elevational side view of the hip pin and plate of FIG. 1;

FIG. 3 is an elevational side view of the hip pin of FIG. 1 showing a cage in unexpanded condition;

FIG. 4 is an elevational side view of the hip pin of FIG. 3 showing the cage in expanded position;

DESCRIPTION OF THE PREFERRED EMBODIMENT

Figure 5:
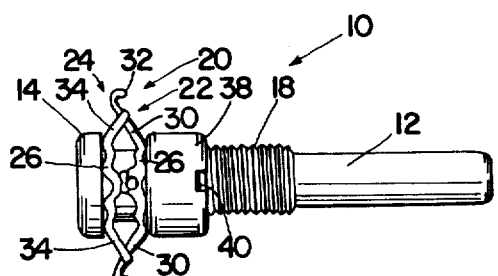
FIG. 5 is a view similar to FIG. 4, in which the pin has been rotated 90 degrees about its longitudinal axis.
Figure 6:
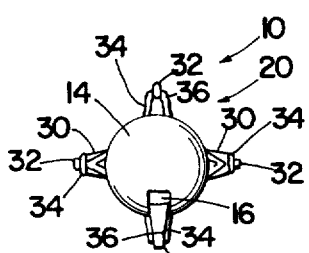
FIG. 6 is an elevational end view of the hip pin of FIG. 1.
Figure 7:
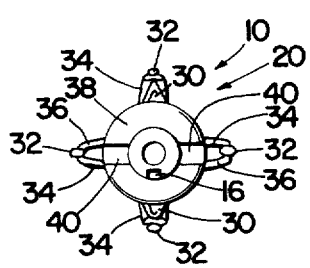
FIG. 7 is an elevational end view of the other end of the hip pin of FIG. 1.
Figure 8:
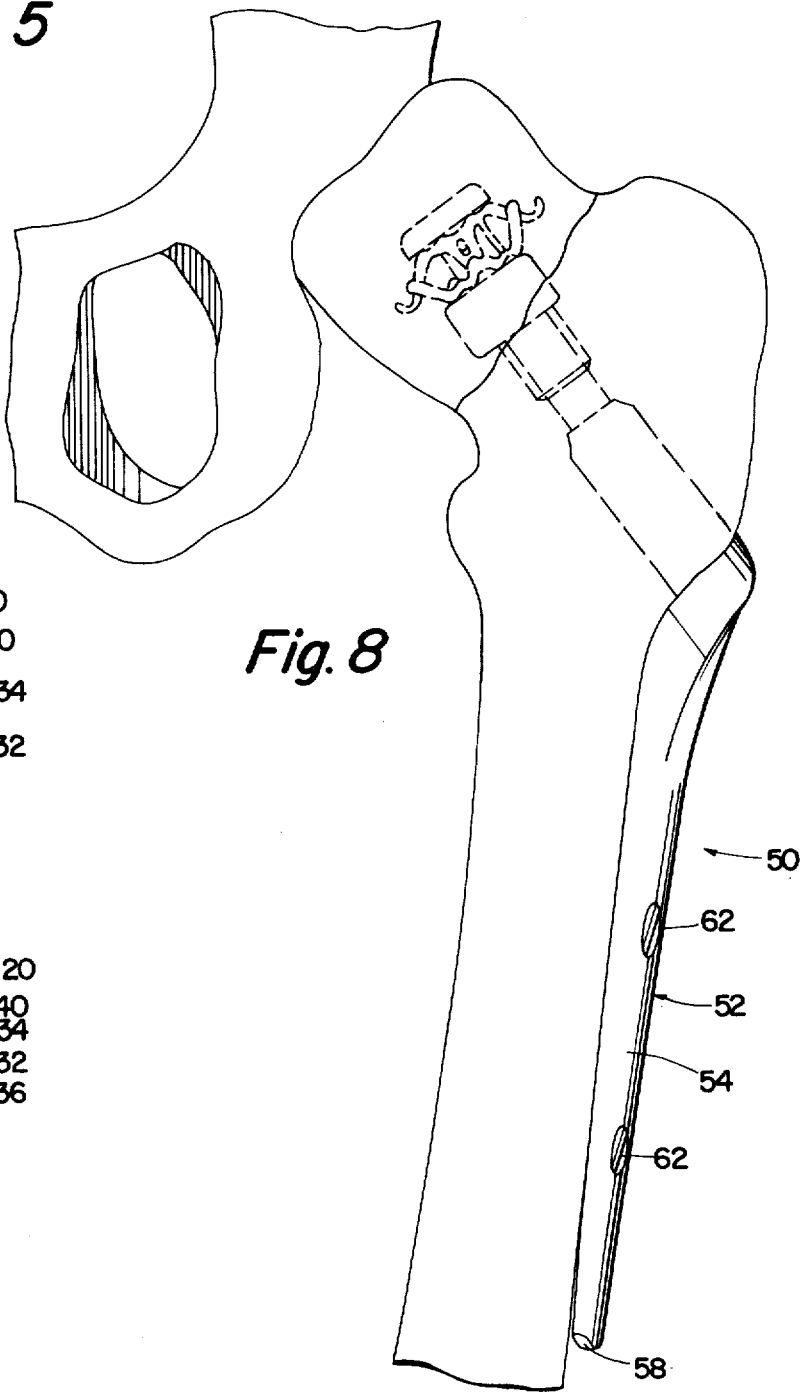
FIG. 8 is a fragmentary perspective view of a portion of a pelvis and fractured femur held together by a hip pin and plate in accordance with an embodiment of the invention.

Referring to FIGS. 1–7, there is shown in intramedullary hip pin 10 and a cortical plate 50, the pin 10 being adapted to be secured within the medulla of the head and neck of the femur, with the plate 50 being adapted to be secured along the lateral cortex of the femur. All parts of the hip pin 10 and the cortical plate 50 are of stainless steel.

The hip pin 10 includes an elongate shaft 12 having an enlarged, flattened end 14. A groove 16 extends longitudinally of the shaft 12, and a plurality of threads 18 are provided near the midpoint of the shaft 12.

Referring particularly to FIGS. 3–7, the pin 10 includes an expansible member 20 in the form of a cage. The cage 20 includes a first section 22 and an opposed, interlocking second section 24. Each of the sections 22, 24 includes a ring 26 having an inwardly extending boss 28 engagable with the groove 16. The ring 26 included as part of the section 22 includes an annular, threaded flange portion 27 extending away from the second section 24. The flange portion 27 is engaged by an extractor instrument (not shown) to remove the cage 20 when healing is complete. When the rings 26 are slipped over the shaft 12, the bosses 28 will prevent rotation of the rings 26 relative to the shaft 12. Each of the sections 22, 24 includes a pair of curved fingers 30 having reversely bent portions, or hooks 32 at the ends. The fingers 30 are spaced 180 degrees from each other about the circumference of the rings 26. Each of the sections 22, 24 includes a pair of legs 34 having openings 36 located near their ends. The openings 36 are approximately the same shape as the cross-section of the fingers 30. The legs 34 are spaced 180 degrees circumferentially about the rings 26 and are spaced 90 degrees from the fingers 30.

When the cage 20 is in unexpanded condition (FIG. 3), the hooks 32 from the section 22 engage the openings 36 of the second section 24. Likewise, the hooks 32 of the second section 24 engage the openings 36 of the first section 22. The bosses 28 are aligned with each other so that the cage 20 can be slipped over the shaft 12 and rotation of the cage 20 with respect to the shaft 12 will be prevented.

The pin 10 also includes a nut 38 having a pair of spaced slots 40. The nut 38 is threaded only for a portion of its length and includes an enlarged-diameter cup portion 41. The nut 38 is engagable with the threads 18. Upon tightening the nut 38 sufficiently, the cup portion 41 will receive the flange portion 27, and the ring 26 of the second section 24 will contact the back face of the end 14 (FIGS. 4–7). If the nut 38 is tightened sufficiently, the sections 22, 24 will be clamped tightly between the end 14 and the nut, thereby compressing the sections 22, 24. Eventually, the cage 20 will be expanded and the fingers 30 will be forced through the openings 36. The legs 34 are stronger than the fingers 30 so that the legs 34 will not be distorted as the sections 22, 24 are compressed. The fingers 30 thus will be forced radially outwardly into the cancellous bone structure of the femur and will cause the pin 10 to be nonmovably secured to the femur. Because the hooks 32 of the first section 22 face in one direction, and because the hooks 32 of the second section 24 face in the other direction, axial, as well as rotational, motion of the pin 10 with respect to the femur will be resisted effectively.

The plate 50 includes an elongate section 52 having a convex surface 54, a concave surface 56, and a rounded end 58. A plurality of openings 60 are formed in the elongate section 52 and are spaced along its length. The openings are adapted to receive bone screws 62 for securing the plate 50 to the shaft of the femur.

The plate 50 also includes a tubular portion 64 located at the end of the elongate section 52 opposite the rounded end 58. The tubular portion 64 is positioned with respect to the longitudinal axis of the elongate section 52 at an angle "A" of approximately 135 degrees. The tubular portion 64 includes an opening 66 extending the length of the tubular portion, as well as an inwardly projecting boss 68. The diameter of the opening 66 and the length of the boss 68 are sized such that the shaft 12 can be inserted into the opening 66, and yet rotation of the shaft 12 relative to the tubular portion 64 will be prevented by engagement between the groove 16 and the boss 68.

ASSEMBLY AND IMPLANTATION

It will be assumed that the femur has experienced a subtrochanteric fracture. Assembly of the pin 10 and implantation of the pin 10 and the plate 50 are carried out as follows:

(1) The cage 20 is secured in place about the shaft 12 by lightly tightening the nut 38.

(2) A one-half inch hole is drilled into the lateral cortex of the femur and through the neck of the femur approximately one inch into the spherical portion of the head.

(3) The groove 16 is located in a lateral orientation with respect to the longitudinal axis of the shaft of the femur and the pin 10 is forced into the head of the femur.

(4) A tubular spanner wrench (not shown) is employed to tighten the nut 38 by engagement with the slots 40. Upon tightening the nut 38 sufficiently, the cage 20 will be expanded into the cancellous bone structure of the femur as has been described already.

(5) The plate 50 is attached to the pin 10 by moving the tubular portion 64 over the shaft 12 with the boss 68 being aligned with the groove 16. The tubular portion 64 will extend a short distance into the previously formed opening and the elongate section 52 will be aligned with the lateral cortex of the femur.

(6) The plate 50 is secured to the shaft of the femur with the bone screws 62 so that the concave surface 56 is in substantial surface-to-surface contact with the shaft.

Due to the enlarged, flattened shape of the end 14 and due to the expansion of the cage 20 into the cancellous bone structure of the femur, forces applied from the pelvis are distributed well and all motion between the hip pin and the femur is prevented. The hip pin 10 is especially effective in preventing perforation of the head of the femur. An additional advantage of the present invention is that the pin 10 cannot rotate with respect to the plate 50 due to the interaction of the groove 16 and the boss 68. Although the pin 10 cannot rotate relative to the tubular portion 64, relative axial movement between them is possible. This allows telescoping of the shaft 12 into the tubular portion 64 so as to keep bone fragments in contact as absorbtion of bone occurs during healing at the fracture site. This is an important advantage of the invention. An additional advantage of the invention is that insertion of the hip pin 10 is exceedingly simple, requiring only a one-half inch hole to be drilled into the lateral cortex of the femur and requiring only the simplest of assembly steps during the implantation process.

Although a preferred embodiment of the invention has been described in some particularity, many variations and modifications in the preferred embodiment may be made without deviating from the invention. Accordingly, it is to be understood that, within the scope of the appended claims, the invention may be practiced otherwise than as specifically described.

What is claimed is:

1. An intramedullary pin, comprising:
   an elongate shaft having a longitudinally extending groove and a threaded portion formed intermediate its ends, the shaft having an enlarged, flattened end;
   an expansible cage adapted to be secured to the shaft, the cage including a first section in the form of a ring encircling the shaft, the ring including a boss extending into the groove, the first section being a generally concave or conical basket including a pair of fingers having reversely bent end portions as well as a pair of legs having openings formed near their ends, the fingers and legs alternating circumferentially of the ring and being spaced 90 degrees from each other, the cage also including a second section, the second section having a generally concave or conical basket the generally concave or conical baskets of the first and second sections having their concave sides facing one another, wherein the fingers extend through openings in the legs to form an interlocking cage;
   the bosses of the first and second sections being axially aligned for engagement with the longitudinal groove in the shaft;
   a nut engagable with the threads on the shaft and with one of the sections such that, upon tightening the nut, the sections are clamped between the nut and the enlarged end and are compressed axially, thereby expanding the fingers radially outwardly of the shaft;
   an elongate section securable to the lateral cortex of the shaft of a femur; and
   a tubular portion positioned at an obtuse angle with respect to the longitudinal axis of the elongate section, the tubular portion adapted to receive the shaft in sliding, non-rotating relationship.

2. An intramedullary pin, comprising:
   an elongate shaft having a longitudinally extending groove and a threaded portion formed intermediate its ends;
   the shaft having an enlarged, flattened end;
   an expansible cage adapted to be secured to the shaft;
   the cage including a first section in the form of a ring encircling the shaft;
   the ring including a boss extending into the groove;
   the first section also including a pair of radially extending fingers having reversely bent end portions and a pair of radially extending legs having openings formed near their ends;
   the fingers and legs alternating circumferentially of the ring and being spaced 90 degrees from each other;
   the cage also including a second section, the second section being substantially identical with the first section and having the reversely bent portions of the fingers interlocking with the openings in the legs of the first section, the openings of the legs in the second section engaging the reversely bent portions of the fingers of the first section, the bosses of the first and second sections being axially aligned for engagement with the longitudinal groove in the shaft; and
   a nut engagable with the threads on the shaft and with one of the sections such that, upon tightening the nut, the sections are clamped between the nut and the enlarged end and are compressed axially, thereby expanding the fingers radially outwardly of the shaft.

* * * * *